United States Patent [19]
DiMatteo et al.

[11] Patent Number: 6,051,010
[45] Date of Patent: *Apr. 18, 2000

[54] METHODS AND DEVICES FOR JOINING TRANSMISSION COMPONENTS

[75] Inventors: Stephen DiMatteo, Seehonk; Brian Estabrook, Foxboro, both of Mass.

[73] Assignee: Ethicon Endo-Surgery, Inc., Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 08/770,550

[22] Filed: Dec. 23, 1996

[51] Int. Cl.$^7$ .................................................. A61B 17/32
[52] U.S. Cl. ............................................. 606/169; 604/22
[58] Field of Search ................................. 606/169, 170, 606/171; 604/22, 27

[56] References Cited

U.S. PATENT DOCUMENTS

| Re. 30,536 | 3/1981 | Perdreaux, Jr. . |
|---|---|---|
| 2,874,470 | 2/1959 | Richards . |
| 3,075,288 | 1/1963 | Balamuth et al. . |
| 3,076,904 | 2/1963 | Kleesattel et al. . |
| 3,213,537 | 10/1965 | Balamuth et al. . |
| 3,368,280 | 2/1968 | Fridman et al. . |
| 3,375,583 | 4/1968 | Blank et al. . |
| 3,488,851 | 1/1970 | Haydu . |
| 3,489,930 | 1/1970 | Shoh . |
| 3,526,036 | 9/1970 | Goof . |
| 3,526,792 | 9/1970 | Shoh . |
| 3,589,012 | 6/1971 | Richman . |
| 3,589,363 | 6/1971 | Banko et al. . |
| 3,593,425 | 7/1971 | Robinson . |
| 3,636,947 | 1/1972 | Balamuth . |
| 3,654,502 | 4/1972 | Carmona et al. . |
| 3,654,540 | 4/1972 | Honig et al. . |
| 3,703,037 | 11/1972 | Robinson . |
| 3,809,977 | 5/1974 | Balamuth et al. . |
| 3,930,173 | 12/1975 | Banko . |
| 3,956,826 | 5/1976 | Perdreaux, Jr. . |
| 4,156,157 | 5/1979 | Mabille . |

(List continued on next page.)

FOREIGN PATENT DOCUMENTS

| 1098003 | 9/1977 | Canada . |
|---|---|---|
| 0 495 634 A2 | 1/1992 | European Pat. Off. . |
| 0578376a1 | 6/1992 | European Pat. Off. . |
| 0666113a1 | 2/1994 | European Pat. Off. . |
| 0 624 346 A2 | 5/1994 | European Pat. Off. . |
| 0 624 346 A3 | 5/1994 | European Pat. Off. . |
| 0695535a1 | 8/1994 | European Pat. Off. . |
| 29 22 239 | 5/1979 | Germany . |
| 37 07 921 A1 | 3/1987 | Germany . |
| 56-108085 | of 1981 | Japan . |

(List continued on next page.)

OTHER PUBLICATIONS

Cooper LaserSonics, Inc., Ultrasonic Surgucal Aspirator NS–100 Operator Manual, 1984, pp. 12, 13, 16, 17, and 29–33.

Cooper LaserSonics, Inc., Ultrasonic Surgical Aspirator NS–100 Operator Manual, 1984, pp. 12, 13, 16, 17, and 29–33.

*Primary Examiner*—William W. Lewis
*Assistant Examiner*—Michael L. Buiz
*Attorney, Agent, or Firm*—Rockey, Milnamow & Katz, Ltd.

[57] ABSTRACT

A coupling structure releasably attaches a plurality of transmission members to each other. Non-vibratory structures hold a second end of the first transmission member in contact with a first end of the second member. A method including the steps of providing a first non-vibratory structure carrying the first transmission member, and providing a second non-vibratory structure carrying the second transmission member. The method also includes the steps of attaching the first non-vibratory structure to the second non-vibratory structure to hold a coupling end of the first transmission rod in contact with a coupling end of the second transmission rod without the use of a threaded connection between the first and second components.

22 Claims, 4 Drawing Sheets

U.S. PATENT DOCUMENTS

| | | |
|---|---|---|
| 4,175,242 | 11/1979 | Kleinschmidt . |
| 4,188,952 | 2/1980 | Loschilov et al. . |
| 4,227,110 | 10/1980 | Douglas et al. . |
| 4,370,131 | 1/1983 | Banko . |
| 4,371,816 | 2/1983 | Wieser . |
| 4,406,284 | 9/1983 | Banko . |
| 4,491,132 | 1/1985 | Aikins . |
| 4,492,574 | 1/1985 | Warrin et al. . |
| 4,526,571 | 7/1985 | Wuchinich ............................... 606/169 |
| 4,674,501 | 6/1987 | Greenberg . |
| 4,750,488 | 6/1988 | Wuchinich et al. . |
| 4,808,153 | 2/1989 | Parisi . |
| 4,816,018 | 3/1989 | Parisi . |
| 4,820,152 | 4/1989 | Warrin et al. . |
| 4,827,771 | 5/1989 | Cary et al. . |
| 4,838,853 | 6/1989 | Parisi ...................................... 606/169 |
| 4,867,141 | 9/1989 | Nakada et al. . |
| 4,870,953 | 10/1989 | DonMicheal et al. . |
| 4,897,079 | 1/1990 | Zaleski et al. . |
| 4,920,954 | 5/1990 | Alliger et al. . |
| 4,922,902 | 5/1990 | Wuchinich et al. . |
| 4,931,047 | 6/1990 | Broadwin et al. . |
| 4,936,281 | 6/1990 | Stasz . |
| 4,974,590 | 12/1990 | Saito . |
| 4,979,952 | 12/1990 | Kubota et al. . |
| 5,011,471 | 4/1991 | Miyazaki et al. . |
| 5,026,387 | 6/1991 | Thomas . |
| 5,047,043 | 9/1991 | Kubota et al. . |
| 5,057,119 | 10/1991 | Clark et al. . |
| 5,059,210 | 10/1991 | Clark et al. . |
| 5,069,664 | 12/1991 | Guess et al. . |
| 5,112,300 | 5/1992 | Ureche . |
| 5,123,903 | 6/1992 | Quaid et al. . |
| 5,151,084 | 9/1992 | Khek . |
| 5,151,085 | 9/1992 | Sakurai et al. . |
| 5,156,143 | 10/1992 | Bocquet et al. ........................ 606/169 |
| 5,158,086 | 10/1992 | Brown et al. . |
| 5,160,317 | 11/1992 | Costin . |
| 5,163,421 | 11/1992 | Bernstein et al. ...................... 606/169 |
| 5,167,725 | 12/1992 | Clark et al. . |
| 5,180,363 | 1/1993 | Idemoto et al. . |
| 5,190,517 | 3/1993 | Zieve et al. . |
| 5,190,557 | 3/1993 | Borodulin et al. . |
| 5,248,296 | 9/1993 | Alliger . |
| 5,263,957 | 11/1993 | Davison . |
| 5,269,309 | 12/1993 | Fort et al. . |
| 5,322,055 | 6/1994 | Davison et al. . |
| 5,324,299 | 6/1994 | Davison et al. . |
| 5,326,342 | 7/1994 | Pflueger et al. . |
| 5,330,502 | 7/1994 | Hassler et al. . |
| 5,342,292 | 8/1994 | Nita et al. . |
| 5,344,420 | 9/1994 | Hilal et al. . |
| 5,346,502 | 9/1994 | Estabrook et al. . |
| 5,380,274 | 1/1995 | Nita . |
| 5,382,228 | 1/1995 | Nita et al. ............................... 606/169 |
| 5,383,888 | 1/1995 | Zvenyatsky et al. . |
| 5,391,180 | 2/1995 | Tovey et al. . |
| 5,403,342 | 4/1995 | Tovey et al. . |
| 5,409,498 | 4/1995 | Braddock et al. . |
| 5,411,519 | 5/1995 | Tovey et al. . |
| 5,417,203 | 5/1995 | Tovey et al. . |
| 5,425,704 | 6/1995 | Sakurai et al. . |
| 5,431,323 | 7/1995 | Smith et al. . |
| 5,438,554 | 8/1995 | Seyed-Bolorforosh et al. . |
| 5,441,512 | 8/1995 | Muller ..................................... 606/169 |
| 5,449,370 | 9/1995 | Vaitekunas . |
| 5,456,401 | 10/1995 | Green et al. . |
| 5,472,439 | 12/1995 | Hurd . |
| 5,472,447 | 12/1995 | Abrams et al. . |
| 5,478,003 | 12/1995 | Green et al. . |
| 5,482,197 | 1/1996 | Green et al. . |
| 5,490,819 | 2/1996 | Nicholas et al. . |
| 5,501,654 | 3/1996 | Failla et al. . |
| 5,507,738 | 4/1996 | Ciervo . |
| 5,507,743 | 4/1996 | Edwards et al. . |
| 5,509,916 | 4/1996 | Taylor . |
| 5,514,157 | 5/1996 | Nicholas et al. . |
| 5,526,815 | 6/1996 | Granz et al. . |
| 5,540,656 | 7/1996 | Pflueger et al. . |
| 5,542,917 | 8/1996 | Nita et al. . |
| 5,546,947 | 8/1996 | Yagami et al. . |
| 5,562,609 | 10/1996 | Brumbach . |
| 5,562,610 | 10/1996 | Brumbach . |
| 5,562,682 | 10/1996 | Oberlin et al. . |
| 5,564,615 | 10/1996 | Bishop et al. . |
| 5,575,799 | 11/1996 | Bolanos et al. . |
| 5,582,588 | 12/1996 | Sakurai et al. . |
| 5,606,974 | 3/1997 | Castellano et al. ................ 128/662.06 |
| 5,607,095 | 3/1997 | Smith et al. . |
| 5,607,450 | 3/1997 | Zvenyatsky et al. . |
| 5,609,601 | 3/1997 | Kolesa et al. . |
| 5,628,743 | 5/1997 | Cimino ........................................ 606/1 |
| 5,649,935 | 7/1997 | Kremer et al. . |

FOREIGN PATENT DOCUMENTS

| | | |
|---|---|---|
| 56-38931 | of 1981 | Japan . |
| 61-265136 | of 1986 | Japan . |
| 2-99049 | of 1990 | Japan . |
| 9-276274 | 10/1997 | Japan . |
| 1388002 A1 | 4/1988 | Russian Federation . |
| WO 91/13591 | 3/1991 | WIPO . |
| WO 92/02658 | 7/1991 | WIPO . |
| 0 495 634 A3 | 1/1992 | WIPO . |
| WO 92/14514 | 2/1992 | WIPO . |
| WO 93/14708 | 1/1993 | WIPO . |
| WO 93/16645 | 1/1993 | WIPO . |
| WO9509570 | 4/1993 | WIPO . |
| WO9510233 | 12/1993 | WIPO . |
| WO 96/29935 | 4/1996 | WIPO . |
| 96 34561 | 5/1996 | WIPO . |

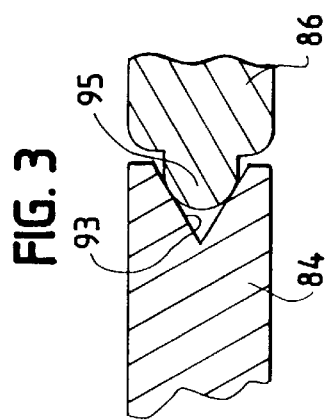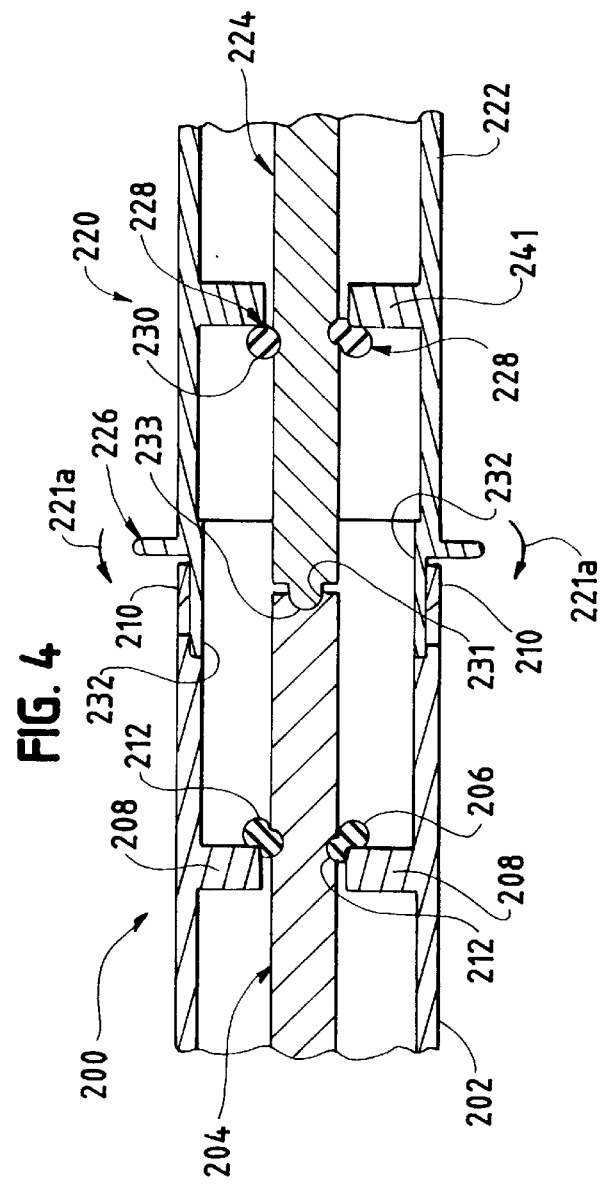

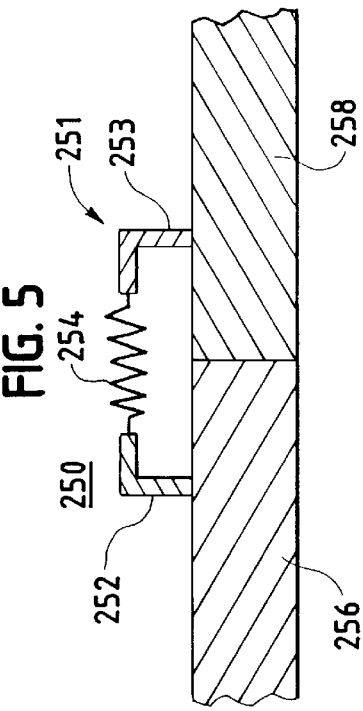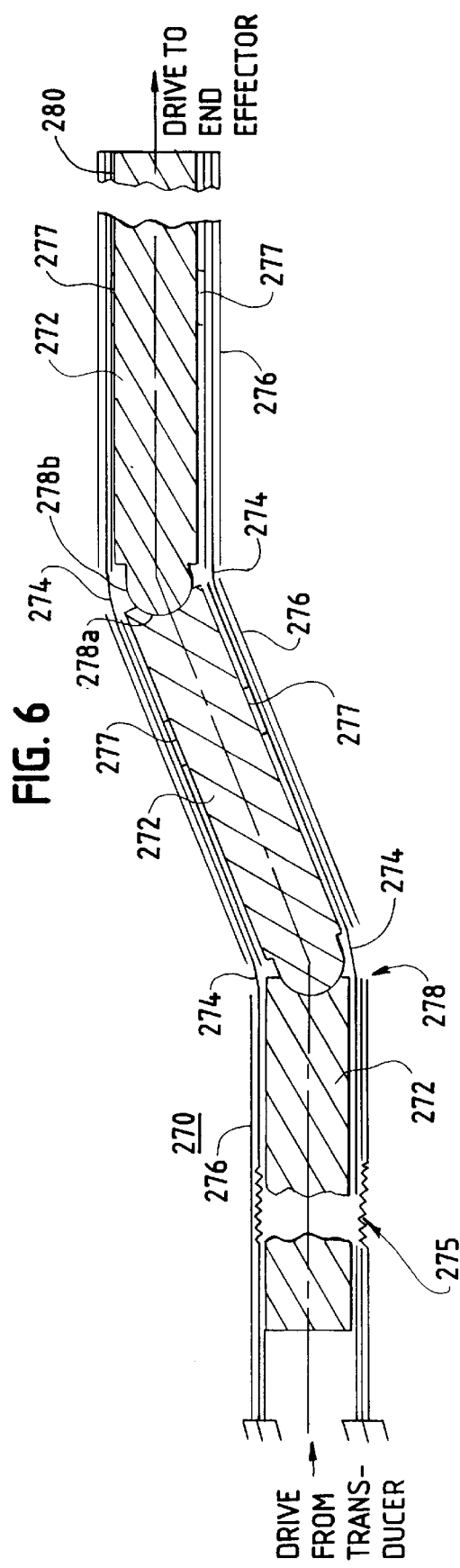

METHODS AND DEVICES FOR JOINING TRANSMISSION COMPONENTS

FIELD OF THE INVENTION

The present invention generally relates to ultrasonic devices. More particularly, it relates to methods and devices for joining a plurality of ultrasonic transmission components by the use of one or more non-vibratory members which carry the ultrasonic transmission components.

BACKGROUND OF THE INVENTION

Ultrasonic transmission devices are frequently used in a variety of applications, such as surgical operations and procedures. Typically, these transmission devices usually include a transducer that converts electrical energy into vibrational motion at ultrasonic frequencies. The vibrational motion is usually transmitted through a transmission component, such as a mounting device, to vibrate a distal end of another transmission component, such as a working member.

The working member is usually attached to the mounting device by a threaded joint. In particular, the proximal end of the working member typically includes a threaded stud that is threaded into a threaded bore of the distal end of the mounting device. The tension between the threaded stud of the working member and the threaded bore of the mounting device provides an axial compression force to prevent the working member and mounting device from separating. However, the threaded bore and the threaded stud are usually costly to fabricate and are typically required to be manufactured within specific tolerance ranges. In addition, it can be difficult to manufacture threaded bores and threaded studs with small diameters.

The working member is usually tightened to the mounting device by using a tool, such a wrench. However, the use of as a wrench may cause the working member to be inadvertently over-tightened, which may tend to strip or damage the threads of the working member and mounting device. When the working member is over-tightened, the working member may be difficult to detach from the mounting device. On the other hand, insufficient tightening of the working member to the mounting device may cause undesired heat build-up of the threaded joints, decrease the transfer of energy across the junction, and cause unwanted transverse motion.

A torque limiting device may also be used to tighten the working member to the mounting device. The torque limiting device is used to assure that a predetermined minimum torque is reached and that a maximum torque is not exceeded when tightening the working member to the mounting device. In one known technique, a separate torque wrench W as illustrated in FIG. 1 may be placed over a working member WM to tighten and untighten the working member WM from a mounting device M of a surgical device. In this technique, the working member WM is attached to the mounting device M by a threaded connection. Once the working member WM is threaded onto the mounting device M, the torque wrench W is then slipped over the working member WM to tighten the working member WM to the mounting device M. A nose cone is then threaded onto the distal end of the handpiece assembly H.

However, it is quite difficult for a user to connect and disconnect the working member from the mounting device in a sterile field when using a separate torque wrench. Further, it may be cumbersome and time consuming to use a torque wrench when changing the working member during an operation or for tightening certain working members to the mounting device. Additionally, the torque wrench can be mislaid or lost and may require calibration or replacement at frequent intervals to ensure accuracy.

Accordingly, there is a need for improved devices and methods to join ultrasonic transmission components. Such devices would further benefit if the transmission components could be readily attached and detached without the use of a separate torque limiting device.

SUMMARY OF THE INVENTION

In view of the above, devices and methods are provided for attaching ultrasonic transmission components together in an operable arrangement without using a separate torque limiting device. The device allows the transmission components to be coupled together through a relatively small contact region and with relatively low coupling forces. The devices further allow transmission components having relatively small diameters to be coupled together. In general, the present invention contemplates use of one or more non-vibratory members for coupling ultrasonic transmission components carried by the non-vibratory members.

An ultrasonic device in accordance with the present invention includes a first transmission member and a second transmission member. A non-vibrating structure provides a preload force to hold an end of the first transmission member in contact with an end of the second member.

A method embodying the principles of the present invention includes the steps of providing a first non-vibratory structure carrying a first transmission member having a first end and a second end, and providing a second non-vibratory structure carrying a second transmission member having a first end and a second end. The method also includes the steps of attaching the first non-vibratory structure to the second non-vibratory structure to provide a preload force to hold one end of the first transmission rod in contact with an end of the second transmission rod without the use of a threaded connection between the first and second transmission members.

It is to be understood that both the foregoing general description and the following detailed description are exemplary and explanatory and are intended to provide further explanation of the invention as claimed.

The invention, together with attendant advantages, will best be understood by reference to the following detailed description of the preferred embodiments of the invention, taken in conjunction with the accompanying drawings.

BRIEF DESCRIPTION OF THE DRAWINGS

FIG. 3 is a fragmentary cross-sectional view of an interface between transmission components of the surgical system illustrated in FIG. 2;

FIG. 4 is a fragmentary cross-sectional view of a second embodiment of a coupling arrangement between two ultrasonic transmission components;

FIG. 5 is a fragmentary cross-sectional view of another coupling arrangement between two ultrasonic transmission components; and FIG. 6 is a cross-sectional view of an articulated ultrasonic waveguide.

DESCRIPTION OF THE PREFERRED EMBODIMENTS

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, the terms and expressions employed herein have been chosen for the purpose of describing the illustrative embodiments of the present invention for the convenience of the reader and are not for the purpose of limitation.

Figure 1:
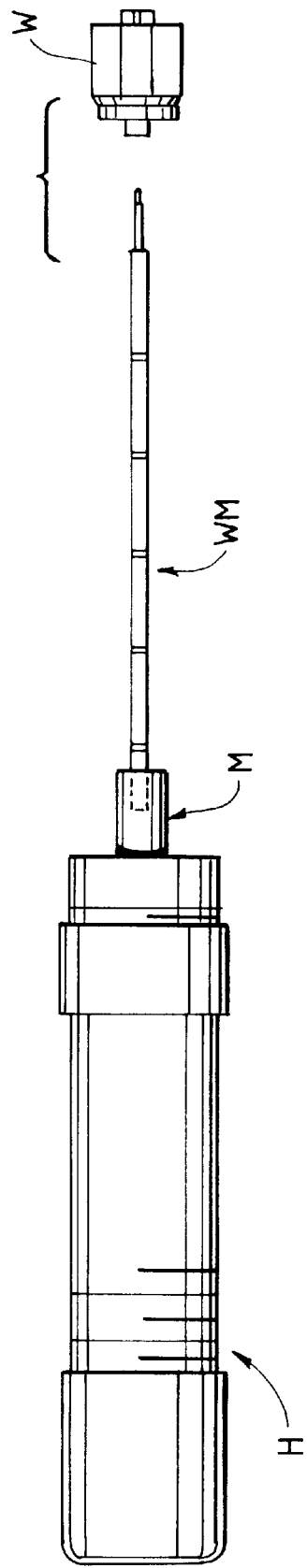
FIG. 1 is a side elevational view of a prior art handpiece assembly of an ultrasonic device.

FIG. 1 shows a side elevational view of a prior art handpiece assembly H. The working member WM is threaded onto the mounting device M. A torque wrench W is slipped over the working member WM to tighten the working member WM to a desired torque to the mounting device M.

Figure 2:
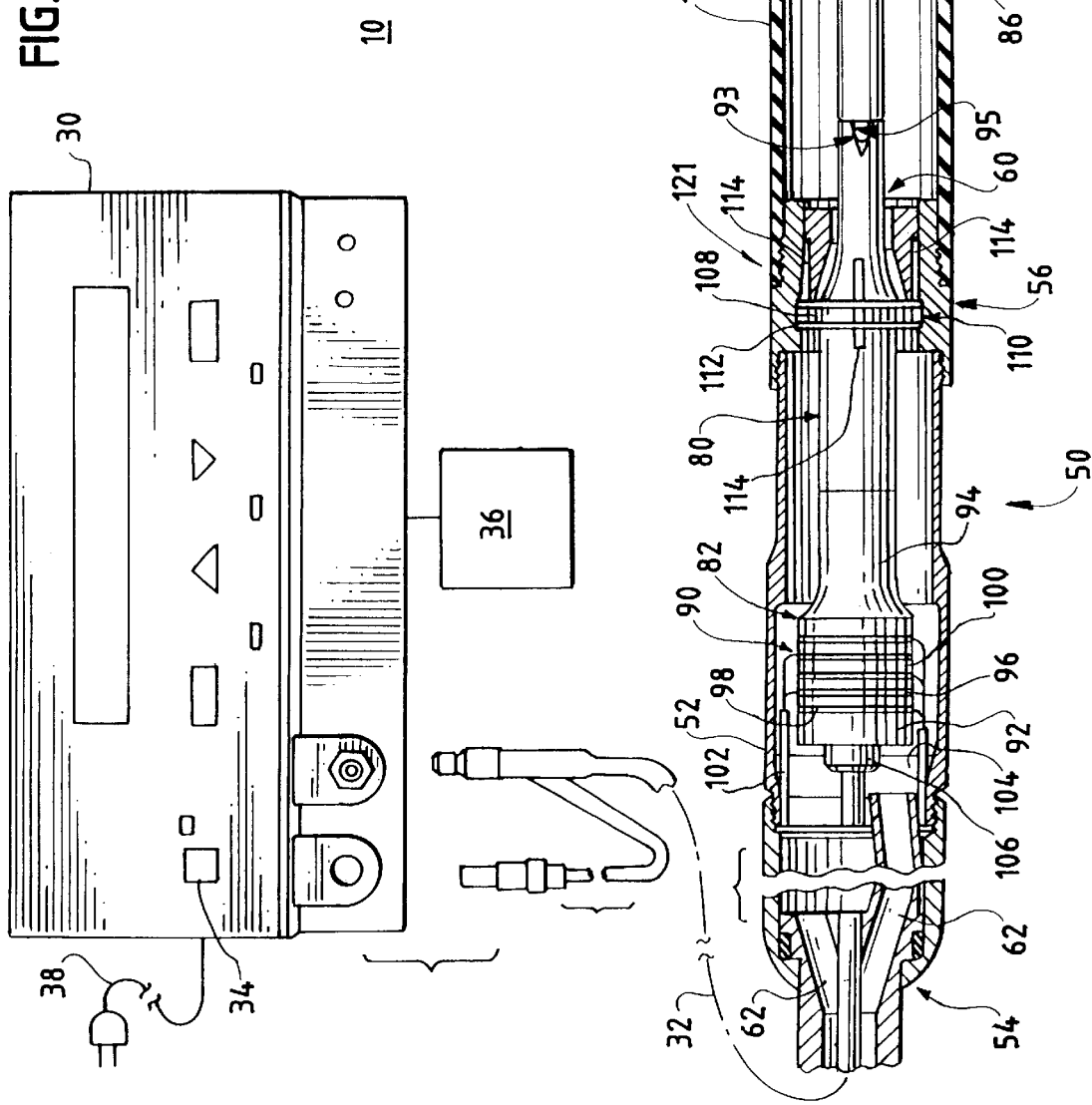
FIG. 2 is a fragmentary view and in partial cross-section of a first embodiment of a surgical system according to the present invention.

Referring now to FIG. 2, an embodiment of the surgical system 10 is illustrated. The surgical system 10 generally includes a generator 30, a handpiece assembly 50, an acoustic or transmission assembly 80, and a surgical tool or instrument 120. The generator 30 sends an electrical signal through a cable 32 at a selected amplitude, frequency, and phase determined by a control system of the generator 30. As will be further described, the signal causes one or more piezoelectric elements of the acoustic assembly 80 to expand and contract, thereby converting the electrical energy into mechanical motion. The mechanical motion results in longitudinal waves of ultrasonic energy that propagate through the acoustic assembly 80 in an acoustic standing wave to vibrate the acoustic assembly 80 at a selected frequency and amplitude. An end effector 88 at the distal end of the acoustic assembly 80 is placed in contact with tissue of the patient to transfer the ultrasonic energy to the tissue. The cells of the tissue in contact with the end effector 88 of the acoustic assembly 80 will move with the end effector 88 and vibrate.

As the end effector 88 couples with the tissue, thermal energy or heat is generated as a result of internal cellular friction within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels when coagulum is below 100° C. Deep coagulation of larger blood vessels results when the effect is prolonged.

The transfer of the ultrasonic energy to the tissue causes other effects including mechanical tearing, cutting, cavitation cell disruption, and emulsification. The amount of cutting as well as the degree of coagulation obtained varies with the vibrational amplitude of the end effector 88, the amount of pressure applied by the user, and the sharpness of the end effector 88. The end effector 88 of the acoustic assembly 80 in the surgical system 10 tends to focus the vibrational energy of the system 10 onto tissue in contact with the end effector 88, intensifying and localizing thermal and mechanical energy delivery.

As illustrated in FIG. 2, the generator 30 includes a control system integral to the generator 30, a power switch 34, and a triggering mechanism 36. The power switch 34 controls the electrical power to the generator 30, and when activated by the triggering mechanism 36, the generator 30 provides energy to drive the acoustic assembly 80 of the surgical system 10 at a predetermined frequency and to drive the end effector 88 at a predetermined vibrational amplitude level. The generator 30 may drive or excite the acoustic assembly 80 at any suitable resonant frequency of the acoustic assembly 80.

When the generator 30 is activated via the triggering mechanism 36, electrical energy is continuously applied by the generator 30 to a transducer assembly 82 of the acoustic assembly 80. A phase lock loop in the control system of the generator 30 monitors feedback from the acoustic assembly 80. The phase lock loop adjusts the frequency of the electrical energy sent by the generator 30 to match a preselected harmonic frequency of the acoustic assembly 80. In addition, a second feedback loop in the control system maintains the electrical current supplied to the acoustic assembly 80 at a preselected constant level in order to achieve substantially constant vibrational amplitude at the end effector 88 of the acoustic assembly 80. The electrical signal supplied to the acoustic assembly 80 will cause the distal end to vibrate longitudinally in the range of, for example, approximately 20 kHz to 100 kHz, and preferably in the range of about 54 kHz to 56 kHz, and most preferably at about 55.5 kHz. The amplitude of the acoustic vibrations at the end effector 88 may be controlled by, for example, controlling the amplitude of the electrical signal applied to the transduction portion 90 of the acoustic assembly 80 by the generator 30.

As noted above, the triggering mechanism 36 of the generator 30 allows a user to activate the generator 30 so that electrical energy may be continuously supplied to the acoustic assembly 80. In one embodiment, the triggering mechanism 36 preferably comprises a foot activating switch that is detachably coupled or attached to the generator 30 by a cable or cord. In another embodiment, a hand switch may be incorporated in the handpiece assembly 50 to allow the generator 30 to be activated by a user.

The generator 30 also has a power line 38 for insertion in an electrosurgical unit or conventional electrical outlet. It is contemplated that the generator 30 may also be powered by a direct current (DC) source, such as a battery. The generator 30 may be any suitable generator, such as Model No. GEN01 available from Ethicon Endo-Surgery, Inc.

Referring still to FIG. 2, the handpiece assembly 50 includes a multi-piece housing or outer casing 52 adapted to isolate the operator from the vibrations of the acoustic assembly 80. The housing 52 is preferably cylindrically shaped and is adapted to be held by a user in a conventional manner, but may be any suitable shape and size which allows it to be grasped by the user. While a multi-piece housing 52 is illustrated, the housing 52 may comprise a single or unitary component.

The housing 52 of the handpiece assembly 50 is preferably constructed from a durable plastic, such as Ultem®. It is also contemplated that the housing 52 may be made from a variety of materials including other plastics (i.e. high impact polystyrene or polypropylene). A suitable handpiece assembly 50 is Model No. HP050, available from Ethicon Endo-Surgery, Inc.

Referring still to FIG. 2, the handpiece assembly 50 generally includes a proximal end 54, a distal end 56, and centrally disposed axial opening or cavity 58 extending longitudinally therein. The distal end 56 of the handpiece assembly 50 is coupled to the surgical instrument 120 and includes an opening 60 configured to allow the acoustic assembly 80 of the surgical system 10 to extend therethrough. The proximal end 54 of the handpiece assembly 50 is coupled to the generator 30 by a cable 32. The cable 32 may include ducts or vents 62 to allow air to be introduced into the handpiece assembly 50 to cool the transducer assembly 82 of the acoustic assembly 80.

The surgical instrument 120 of the surgical system 10 is preferably couplable to the distal end 56 of the handpiece assembly 50. The surgical instrument 120 generally includes a housing or adapter 122, a compliant support 124, and a sheath or tubular member 128. The proximal end 121 of the housing 122 of the surgical instrument 120 is threaded onto the distal end 56 of the handpiece assembly 50. It is also contemplated that the surgical instrument 120 may be coupled to the handpiece assembly 50 by any suitable means, such as a snap-on connection or the like, without departing from the spirit and scope of the present invention.

The housing 122 of the surgical instrument 120 is preferably cylindrically shaped and has an opening 123 at its distal end 126 to allow the acoustic assembly 80 to extend therethrough. The housing 122 may be fabricated from Ultem®. It is contemplated that the housing 122 may be made from any suitable material without departing from the spirit and scope of the invention.

The sheath 128 of the surgical instrument 120 is attached to the distal end 126 of the housing 122. The sheath 128 has an opening extending longitudinally therethrough. The sheath 128 may be fabricated from stainless steel or any other suitable material. Alternatively, polymeric material may surround the transmission rod 86 to isolate it from outside contact.

Referring still to FIG. 2, the acoustic assembly 80 generally includes a transducer stack or assembly 82, a mounting device 84, a transmission rod or waveguide 86, and an end effector or applicator 88. The transducer assembly 82, mounting device 84, a transmission rod 86, and the end effector 88 may be acoustically tuned such that the length of each component is an integral number of one-half system wavelengths ($N\lambda/2$) where the system wavelength $\lambda$ is the wavelength of a preselected or operating longitudinal vibration frequency f of the acoustic assembly 80. It is also contemplated that the acoustic assembly 80 may incorporate any suitable arrangement of acoustic elements. For example, the acoustic assembly 80 may comprise a transducer assembly and an end effector (i.e., the acoustic assembly 80 may be configured without a mounting device and a transmission rod). In one embodiment, the transducer 82 and mounting device 84 are carried by the handpiece assembly 50, and the transmission rod 86 and end effector 88 are carried by the surgical instrument 120.

The transducer assembly 82 of the acoustic assembly 80 converts the electrical signal from the generator 30 into mechanical energy that results in longitudinal vibrating motion of the end effector 88 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. For example, a minimum or zero crossing in the vibratory motion standing wave is generally referred to as a node (i.e., where axial motion is usually minimal and radial motion is usually small), and an absolute value maximum or peak in the standing wave is generally referred to as an antinode. The distance between an antinode and its nearest node is one-quarter wavelength ($\lambda/4$).

As shown in FIG. 2, the transducer assembly 82 of the acoustic assembly 80, which is known as a "Langevin stack", generally includes a transduction portion 90, a first resonator 92, and a second resonator 94. The transducer assembly 82 is preferably an integral number of one-half wavelengths system ($N\lambda/2$) in length. It is to be understood that the present invention may be alternatively configured to include a transducer assembly comprising a magnetostrictive, electromagnetic or electrostatic transducer.

The distal end the first resonator 92 is connected to the proximal end of the transduction section 90, and the proximal end of the second resonator 94 is connected to the distal end of the transduction portion 90. The first and second resonators 92 and 94 are preferably fabricated from titanium, aluminum, steel, or any other suitable material. The first and second resonators 92 and 94 have a length determined by a number of variables, including the thickness of the transduction section 90, the density and modulus of elasticity of material used in the resonators 92 and 94, and the fundamental frequency of the transducer assembly 82. The second resonator 94 may be tapered inwardly from its proximal end to its distal end to amplify the ultrasonic vibration amplitude.

The transduction portion 90 of the transducer assembly 82 preferably comprises a piezoelectric section of alternating positive electrodes 96 and negative electrodes 98, with piezoelectric elements 100 alternating between the electrodes 96 and 98. The piezoelectric elements 100 may be fabricated from any suitable material, such as lead zirconate, lead titanate, or ceramic crystal material. Each of the piezoelectric elements 100, negative electrodes 98, and positive electrodes 96 may have a bore extending through the center. The positive and negative electrodes 96 and 98 are electrically coupled to wires 102 and 104, respectively. The wires 102 and 104 transmit the electrical signal from the generator 30 to electrodes 96 and 98.

As shown in FIG. 2, the piezoelectric elements 100 are held in compression between the first and second resonators 92 and 94 by a bolt 106. The bolt 106 preferably has a head, a shank, and a threaded distal end. The bolt 106 is inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94.

The piezoelectric elements 100 are energized in response to the electrical signal supplied from the generator 30 to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing high frequency longitudinal waves of ultrasonic energy. The ultrasonic energy is transmitted through the acoustic assembly 80 to the end effector 88.

The mounting device 84 of the acoustic assembly 80 has a proximal end, a distal end, and may have a length substantially equal to an integral number of one-half system wavelengths. The proximal end of the mounting device 84 is preferably axially aligned and coupled to the distal end of the second resonator 94 by an internal threaded connection near an antinode. It is also contemplated that the mounting device 84 may be attached to the second resonator 94 by any suitable means, and that the second resonator 94 and mounting device 84 may be formed as a single or unitary component.

The mounting device 84 is coupled to the housing 52 of the handpiece assembly 50 near a node. (For purposes of this disclosure, the term "near" is defined to mean "exactly at" or "in close proximity to".) The mounting device 84 may also include an integral ring 108 disposed about its periphery. The integral ring 108 is preferably disposed in an annular groove 110 formed in the housing 52 of the handpiece assembly 50 to couple the mounting device 84 to the housing 58. A compliant member or material 112, such as a pair of silicon O-rings attached by standoffs, may be placed between the annular groove 110 of the housing 52 and the integral ring 108 of the mounting device 84 to reduce or prevent ultrasonic vibration from being transmitted from the mounting device 84 to the housing 52.

The mounting device 84 may be secured in a predetermined axial position by a plurality of pins 114, preferably four. The pins 114 are disposed in a longitudinal direction 90 degrees apart from each other around the outer periphery of the mounting device 84. The pins 114 are coupled to the housing 52 of the handpiece assembly 50 and are disposed through notches in the integral ring 108 of the mounting device 84. The pins 114 are preferably fabricated from stainless steel.

The mounting device 84 is preferably configured to amplify the ultrasonic vibration amplitude that is transmitted through the acoustic assembly 80 to the distal end of the end effector 88. In one preferred embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 may be any suitable shape, such as a stepped horn, a conical horn, an exponential horn, or the like.

The distal end of the mounting device 84 is configured to interface or engage with the proximal end of the transmission rod 86. As shown in FIG. 3, the distal end of the mounting device 84 preferably has a mating or coupling surface 93 that is axially aligned with a mating or coupling surface 95 of the proximal end of the transmission rod 86. The mating surface 93 of the mounting device 84 has a non-threaded cavity or bore that is substantially conically or wedge shaped. It is also contemplated that the mating surface 93 of the mounting device 84 be formed as a convex or partially curved surface.

The mating surface 95 of the transmission rod 86 has a non-threaded axially extending member or projection. The mating surface 95 is preferably substantially spherically shaped. It is contemplated that the surfaces 93,95 could be interchanged. For example, the mounting device 84 may have a non-threaded projection at its distal end and the transmission rod 86 may have a non-threaded cavity at its proximal end. Other suitable mating surfaces having different non-threaded surfaces could be used without departing from the spirit and scope of the present invention. The mating surfaces 93,95 of the mounting device 84 and transmission rod 86 may also be coated with titanium nitride (TiN) to improve wear life.

The mating surface 93 of the mounting device 84 and the mating surface 95 of the transmission rod 86 are forced together axially so that the junction or point of contact is preferably near an antinode. Preferably, a minimal contact area exists between the mating surfaces 93,95. A coupling force between the mating surfaces 93,95 is created when the handpiece assembly 50 is coupled to the surgical instrument 120. The handpiece assembly 50 and the surgical instrument 120 are preferably coupled near a vibrational antinode because it is the point of minimum stress and therefore requires the least preload force.

The mating surfaces 93,95 of the transmission rod 86 and the mounting device 84 provide a socket arrangement which is self-aligning and self-centering. The socket arrangement also allows slight non-axial alignment of the transmission rod 86 and the mounting device 84. The contact region or area between the mating surfaces 93,95 efficiently transfers mechanical or ultrasonic vibration across the junction between them. The contact region between the mating surfaces 93,95 has a relatively small area. As a result, a moderate or relatively low preload force can hold the transmission rod 86 and the mounting device 84 together. For example, because of the shape of the interacting surfaces 93,95, an axial pre-load force between 5–25 pounds may be sufficient to hold the mounting device 84 and transmission rod 86 together. This is a lower force than is often required to reliably couple together threaded ultrasonic elements.

Referring again to FIG. 2, the transmission rod 86 includes a support or retention member. The retention member preferably includes an integral ring or flange 130 disposed around its periphery. It is also contemplated that the retention member may include a number of suitable configurations, such as an O-ring fixedly attached to a groove or the periphery of the transmission rod 88.

A compliant member 124 is preferably positioned between the integral ring 130 of the transmission rod 86 and the distal end 126 of the housing 122 of the surgical tool 120. The compliant member 124 preferably isolates the housing 122 of the surgical instrument 120 from the ultrasonic vibrations of the transmission rod 86. The compliant member 124 is preferably an O-ring fabricated from silicone or polyterafluroethylene (PTFE) and having a low spring rate (i.e., k rate (k)). In an alternative embodiment, the compliant member 124 preferably consists of a thin layer of compliant material with a high or low k rate on a conventional metal or plastic coil or disk spring.

The compliant member 124 preferably contacts the transmission rod 86 at a plane perpendicular to the axis of the transmission rod 86 to provide a compression force perpendicular to the radial motion near or at the node to minimize the loss of ultrasonic power caused by the vibration of the compliant member 124. This configuration also allows the transmission rod 86 to be rotated relative to the handpiece assembly 50 without removing it or loosening the connection between the handpiece assembly 50 and the surgical instrument 120.

To couple the surgical instrument 120 to the handpiece assembly 50, the surgical instrument 120 is preferably threaded onto the distal end 56 of the handpiece assembly 50 bringing the mounting surface 95 of the transmission rod 86 into communication or contact with the mounting surface 93 of the mounting device 84. Alternate arrangements, such as a twist-lock fitting, are also within the spirit and scope of the present invention.

When the surgical instrument 120 is attached to the handpiece assembly 50, the compliant member 124 is compressed to create an attachment force or preload force. The compliant member 124 preferably has a low spring rate (k) to provide a preload force of contact between the mounting device 84 and the transmission rod 86 that is substantially the same regardless of the tolerances of the components or the manner that the surgical instrument 120 is attached to the handpiece assembly 50. It is contemplated that the surgical instrument 120 may be attached to the handpiece assembly 50 by any suitable means, such as, for example, a threaded or snap-on connection, to compress the compliant member, such as, for example, springs, O-rings and the like, to create the preload force.

Referring again to FIG. 2, the transmission rod 86 of the acoustic assembly 80 may have a length substantially equal to an integer number of one-half system wavelengths (Nλ/2). The transmission rod 86 is preferably fabricated from a solid core shaft constructed out of material which propagates ultrasonic energy efficiently, such as titanium alloy (i.e., Ti-6A1-4V) or an aluminum alloy. As those skilled in the art will recognize, the transmission rod 86 may be fabricated from other suitable materials. The transmission rod 86 may also amplify the mechanical vibrations transmitted through the transmission rod 86 to the end effector 88 as is well known in the art.

The transmission rod 86 includes stabilizing silicone rings or compliant supports 116 (one being shown) positioned at a plurality of nodes. The silicone rings 116 dampen undesirable vibration and isolate the ultrasonic energy from a sheath 128 of the surgical instrument 120 assuring the flow of ultrasonic energy in a longitudinal direction to the distal end of the end effector 88 with maximum efficiency.

The distal end of the transmission rod 86 is coupled to the proximal end of the end effector 88 by an internal threaded connection, preferably near an antinode. It is contemplated that the end effector 88 may be attached to the transmission rod 86 by any suitable means, such as a welded joint or the like. Although the end effector 88 may be detachable from the transmission rod 86, it is also contemplated that the end effector 88 and transmission rod 86 may be formed as a single unit.

The end effector 88 may have a distal region 88b having a smaller cross-section area than a proximal region 88a thereof, thereby forming a vibrational amplitude step-up junction. The step-up junction acts as velocity transformer as known in the art, increasing the magnitude of the ultrasonic vibration transmitted from the proximal region 88a to the distal region 88b of the end effector 88.

The end effector 88 may have a length substantially equal to an integral multiple of one-half system wavelengths (Nλ/2). The distal tip of the end effector 88 is disposed at an antinode where the maximum longitudinal deflection occurs. When the transducer assembly 82 is energized, the distal end of the end effector 88 is configured to move longitudinally in the range of 10 to 500 microns peak-to-peak, and preferably in the range of 30 to 100 microns at a predetermined vibrational frequency, and most preferably at about 90 microns.

The end effector 88 is preferably made from a solid core shaft constructed of material which propagates ultrasonic energy, such as a titanium alloy (i.e., Ti-6A1-4V) or an aluminum alloy. As those skilled in the art will recognize, the end effector 88 may be fabricated from other suitable materials. The distal end of the end effector 88 may be any suitable shape to transfer the ultrasonic energy to the tissue of a patient. It is also contemplated that the end effector 88 may have a surface treatment to improve the delivery of energy and desired tissue effect. For example, the end effector 88 may be micro-finished, coated, plated, etched, grit-blasted, roughened or scored to enhance coagulation in tissue. Additionally, the end effector may be shaped to enhance its energy transmission characteristics. For example, the end effector 88 may be blade shaped, hook shaped, or ball shaped.

Referring now to FIG. 4, another embodiment of a coupling arrangement between a first ultrasonic device 200 and a second ultrasonic device 220 is illustrated. The first ultrasonic device 200 generally includes a housing or sheath 202, a transmission component or member 204, and an elastomeric or compliant material 206. The housing 202 of the first ultrasonic device 200 preferably includes an inwardly projecting ring 208 and coupling members 210. The housing 202 preferably surrounds the transmission member 204 to isolate the transmission component 204 from contact by a user.

The housing 202 of the first ultrasonic device 200 is preferably cylindrically shaped. It is contemplated that the housing 202 may be any suitable configuration without departing from the spirit and scope of the invention. The housing 202 may be constructed from any suitable material, preferably Ultem®.

The second ultrasonic device 220 generally includes a housing or sheath 222, a transmission component or member 224, a release mechanism 226, and a elastomeric or compliant material 228. The housing 222 of the second ultrasonic device 220 preferably includes an inwardly projecting ring 230 and coupling members 232. The housing 222 preferably surrounds the transmission component 224 to isolate the transmission member 224 from contact by a user.

The housing 222 of the second ultrasonic device 220 is preferably cylindrically shaped. It is contemplated that the housing 222 may be any suitable configuration. The housing may also be fabricated from any suitable material, preferably Ultem®.

The housings 202,222 of the first and second ultrasonic devices 200,220 are couplable to each other by the coupling members 210,232. The coupling members 210,232 preferably comprise interlocking members to secure the housings 202,222 together. Preferably, the coupling members 210,232 snap together when the housings 202,222 are slid together axially. It is contemplated that the housings 202,222 may be attached by any suitable releasable latching or locking mechanism. The housings 202,222 may be disconnected by pressing the release mechanism 226 while pulling the housings 202,222 apart. When the release mechanism 222 is pressed in the direction of arrows 221a, the release mechanism 222 disconnects the coupling members 210,232.

The transmission members 204,224 of the first and second ultrasonic devices 200,220 preferably have mating surfaces or regions 231,233 that are adapted to be brought into communication or contact with each other, preferably near or at an antinode. The mating surfaces or regions 231,233 are substantially similar to the mating surfaces of the transmission rod 86 and the mounting device 84 as described above. As such, further description of the mating surfaces 231,233 of the transmission members 204,224 are unnecessary for a complete understanding of this embodiment.

The compliant members 206,228 each comprise an O-ring that is located in grooves 212 and 241 disposed about the periphery of each transmission member 204,224. The complaint members 206,228 are attached to the grooves 212,241 by mechanical interference or an adhesive. In one preferred embodiment, the compliant members 206,228 are secured to the transmission components 206,228 by the adhesion of silicone created by a molding process as is known in the art. The compliant members 206,228 position and support the transmission members 204,224 within the housings 202,232 to reduce the conduction of vibration into the housings 202,232 and minimize energy loss due to heating or noise.

When the ultrasonic devices 200,220 are coupled to each other, a preload force is created between the transmission members 204,224 by the compliant members 206,228 which are compressed or stretched elastically. It is also contemplated that although the support structure is illustrated as an external element, it could be located within a lumen within the transmission members 204,224. For example, the transmission member 204 may be inserted into a lumen of the transmission member 224 and held together by a press fit or floating pin.

Referring now to FIG. 5, another embodiment of a coupling arrangement 250 for joining ultrasonic transmission components is illustrated. The coupling arrangement 250 generally includes a non-vibrating structure support (generally indicated at 251), a first transmission component or member 256, and a second transmission component or member 258. The non-vibrating structure 251 preferably includes a first portion 252, a second portion 253, and a coupling mechanism 254 for generating a preload force. The first portion 252 of the non-vibrating structure is preferably resiliently coupled to the first transmission component 256 near a node, and the second portion 253 of the non-vibrating structure is resiliently coupled to the second transmission component 258 near a node. The first portion 252 and second portion 253 are isolated from the transmission components 256,258 by compliant support material.

The first and second transmission components 256,258 are joined to or held together near an antinode to minimize the preload force required to hold them together. The coupling mechanism 254 generates sufficient preload force to couple the transmission components 256,258 together. The coupling mechanism 254 may be provided by any suitable mechanism, such as springs, living snaps, pneumatics, magnetic, suction/vacuum from an operating room, mechanical over center toggle, ¼ turn threaded fitting, and the like.

Referring now to FIG. 6, a preferred embodiment of an articulated or flexible ultrasonic transmission or waveguide assembly 270 is illustrated. The waveguide assembly 270 includes a plurality of transmission components or members 272, tension wires 274, a spring or adjustable tensioner 275, a tube-like sheath or tension wire guide 276 that surrounds the transmission components 274, and elastomeric attachments 277.

The adjacent ones of the transmission components 272 are joined or held together near an antinode of vibration. The transmission components 272 each have a mating surface or region 278a and 278b that is substantially similar to the mating surfaces of the transmission members 204,224 described above. As such, further description of the mating surface 278 of the transmission components 272 is unnecessary for a complete understanding of this embodiment.

The tension wire 275 of the waveguide assembly 270 extends through the tension wire guide. The tension wire 275 provides a force to create a substantially uniform contact force between the mating surfaces 278a and 278b of the transmission components 272 when tightened. The tension wires 275 may be tightened or loosened through the adjustable tensioner 275 in order to change the angles between the transmission components 274, allowing the waveguide assembly 270 to be configured in a desired shape. The transmission component 272 may be positioned in a wide range of connected angles with respect to each other. The waveguide assembly 270 may be attached or coupled to another transmission component 280.

The methods and devices of present invention allow transmission components to be joined without using an external torque limiting device. Adjacent ones of the transmission components are joined together near or at an antinode. The transmission components are maintained in contact by a preloaded force created by a non-vibrating structure. The area of contact between the transmission components may be relatively small and the transmission components may also have relatively small diameters.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all aspects only as illustrative and not restrictive, and the scope of the invention is, therefore, indicated by the appended claims rather than the foregoing description. All changes that come within the meaning and range of equivalency of the claims are to be embraced within their scope.

What is claimed is:

1. An ultrasonic surgical device comprising:

a transducer assembly adapted to vibrate at an ultrasonic frequency in response to electrical energy;

a mounting device having a first end and a second end, the mounting device having a length which is substantially equal to an integral number of one-half wavelengths of the ultrasonic frequency, the mounting device being adapted to receive the ultrasonic vibration from the transducer assembly and to transmit the ultrasonic vibration from the first end to the second end of the mounting device, the first end of the mounting device being coupled to the transducer assembly near an antinode;

a transmission rod having a first end and a second end, the transmission rod having a length which is substantially equal to an integral multiple of one-half wavelengths of the ultrasonic frequency, the transmission rod being adapted to receive the ultrasonic vibration from the mounting device and to transmit the ultrasonic vibrations from the first end to the second end of the transmission rod, the first end of the transmission rod being coupled to the second end of the mounting device by a non-threaded interface near an antinode; and an end effector having a first end and a second end, the end effector being adapted to receive the ultrasonic vibrations from the transmission rod and transmit the vibrations from the first end to the second end of the end effector; the first end of the end effector being coupled to the second end of the transmission rod, and the second end of the end effector being disposed near an antinode.

2. The device of claim 1 wherein the second end of the mounting device includes a non-threaded cavity.

3. The device of claim 1 wherein the first end of the transmission rod has a non-threaded projection.

4. The device of claim 1 further comprising a handpiece assembly coupled to the mounting device near a node of vibration.

5. The device of claim 4 wherein one end selected from the first end of the transmission rod and the second end of the mounting rod includes a cavity, wherein the other end selected therefrom includes a projection projecting into the cavity, and wherein the device further comprises at least one compliant member arranged to force the projection into the cavity, so as to define the non-threaded interface.

6. The device of claim 5 wherein the first end of the transmission rod includes the cavity and wherein the second end of the mounting rod includes the projection.

7. The device of claim 4 wherein the first end of the transmission rod includes a substantially conically or wedge-shaped cavity, wherein the second end of the mounting rod includes a projection projecting into the cavity and mating with the first end of the transmission rod wherein the device further includes a compliant member positioned at the second end of the transmission rod and arranged to force the projection into the cavity, so as to define the non-threaded interface.

8. The device of claim 7 wherein the projection is substantially spherical where mating with the first end of the transmission rod.

9. The device of claim 1 further comprising an adapter coupled to the transmission rod near a node of vibration.

10. The device of claim 9 wherein one end selected from the first end of the transmission rod and the second end of the mounting rod includes a cavity, wherein the other end selected therefrom includes a projection projecting into the cavity, and wherein the device further comprises at least one compliant member arranged to force the projection into the cavity, so as to define the non-threaded interface.

11. The device of claim 10 wherein the first end of the transmission rod includes the cavity and wherein the second end of the mounting rod includes the projection.

12. The device of claim 9 wherein the first end of the transmission rod includes a substantially conically or wedge-shaped cavity, wherein the second end of the mounting rod includes a projection projecting into the cavity and mating with the first end of the transmission rod wherein the device further includes a compliant member positioned at the second end of the transmission rod and arranged to force the projection into the cavity, so as to define the non-threaded interface.

13. The device of claim 12 wherein the projection is substantially spherical where mating with the first end of the transmission rod.

14. The device of claim 1 further comprising a generator to energize the transducer assembly.

15. The device of claim 14 wherein one end selected from the first end of the transmission rod and the second end of the mounting rod includes a cavity, wherein the other end selected therefrom includes a projection projecting into the cavity, and wherein the device further comprises at least one compliant member arranged to force the projection into the cavity, so as to define the non-threaded interface.

16. The device of claim 15 wherein the first end of the transmission rod includes the cavity and wherein the second end of the mounting rod includes the projection.

17. The device of claim 14 wherein the first end of the transmission rod includes a substantially conically or wedge-shaped cavity, wherein the second end of the mounting rod includes a projection projecting into the cavity and mating with the first end of the transmission rod wherein the device further includes a compliant member positioned at the second end of the transmission rod and arranged to force the projection into the cavity, so as to define the non-threaded interface.

18. The device of claim 17 wherein the projection is substantially spherical where mating with the first end of the transmission rod.

19. The device of claim 1 wherein one end selected from the first end of the transmission rod and the second end of the mounting rod includes a cavity, wherein the other end selected therefrom includes a projection projecting into the cavity, and wherein the device further comprises at least one compliant member arranged to force the projection into the cavity, so as to define the non-threaded interface.

20. The device of claim 19 wherein the first end of the transmission rod includes the cavity and wherein the second end of the mounting rod includes the projection.

21. The device of claim 1 wherein the first end of the transmission rod includes a substantially conically or wedge-shaped cavity, wherein the second end of the mounting rod includes a projection projecting into the cavity and mating with the first end of the transmission rod wherein the device further includes a compliant member positioned at the second end of the transmission rod and arranged to force the projection into the cavity, so as to define the non-threaded interface.

22. The device of claim 21 wherein the projection is substantially spherical where mating with the first end of the transmission rod.

* * * * *

UNITED STATES PATENT AND TRADEMARK OFFICE
CERTIFICATE OF CORRECTION

PATENT NO. : 6,051,010
DATED : April 18, 2000
INVENTOR(S) : Stephen Dimatteo, et al.

It is certified that error appears in the above-indentified patent and that said Letters Patent is hereby corrected as shown below:

In claim 1, line 22, kindly insert --detachably-- after "coupled".

Signed and Sealed this

Twenty-seventh Day of March, 2001

Attest:

NICHOLAS P. GODICI

Attesting Officer

Acting Director of the United States Patent and Trademark Office